(12) United States Patent
Hsieh

(10) Patent No.: US 11,083,669 B2
(45) Date of Patent: Aug. 10, 2021

(54) ACUPRESSURE SLEEVE HAVING FAR INFRARED AND NEGATIVE ION DOUBLE EFFECT ENERGY

(71) Applicant: HOMEWAY TECHNOLOGY CO., LTD., Tainan (TW)

(72) Inventor: Chin-Hsing Hsieh, Tainan (TW)

(73) Assignee: HOMEWAY TECHNOLOGY CO., LTD., Tainan (TW)

( * ) Notice: Subject to any disclaimer, the term of this patent is extended or adjusted under 35 U.S.C. 154(b) by 249 days.

(21) Appl. No.: 16/356,096

(22) Filed: Mar. 18, 2019

(65) Prior Publication Data
US 2020/0016031 A1 Jan. 16, 2020

(30) Foreign Application Priority Data
Jul. 13, 2018 (TW) .................................. 107209479

(51) Int. Cl.
*A61H 39/04* (2006.01)
*A61F 13/10* (2006.01)
*A61F 13/00* (2006.01)

(52) U.S. Cl.
CPC .......... *A61H 39/04* (2013.01); *A61F 13/107* (2013.01); *A61F 2013/0028* (2013.01); *A61H 2201/165* (2013.01); *A61H 2201/1635* (2013.01)

(58) Field of Classification Search
CPC ........ A61H 39/00; A61H 39/02; A61H 39/04; A61F 13/107; A41D 13/0015
See application file for complete search history.

(56) References Cited

U.S. PATENT DOCUMENTS

| 5,601,598 A * | 2/1997 | Fisher ..................... A61B 17/00 131/270 |
| 2012/0131720 A1 * | 5/2012 | Nordstrom ........... A41D 31/185 2/69 |
| 2014/0298560 A1 * | 10/2014 | Bailey, II ........... A41D 13/0015 2/69 |

* cited by examiner

*Primary Examiner* — Tuan V Nguyen

(57) ABSTRACT

An acupressure sleeve for applying acupressure to predetermined acupoints on an arm of a user includes a sleeve body and an acupressure unit. The sleeve body is configured to elastically and tightly press against the arm of the user when the acupressure sleeve is worn by the user. The sleeve body has a fiber substrate, and a plurality of far-infrared particles and a plurality of negative ion particles blended in the fiber substrate. The acupressure unit includes a plurality of acupressure protrusions protruding from the fiber substrate into an interior of the sleeve body and configured to apply acupressure to the arm of the user at positions respectively corresponding to the predetermined acupoints.

8 Claims, 3 Drawing Sheets

ACUPRESSURE SLEEVE HAVING FAR INFRARED AND NEGATIVE ION DOUBLE EFFECT ENERGY

CROSS-REFERENCE TO RELATED APPLICATION

This application claims priority of Taiwanese Patent Application No. 107209479, filed on Jul. 13, 2018.

FIELD

The disclosure relates to a sleeve worn on an arm of a user, and more particularly to an acupressure sleeve having far infrared and negative ion double effect energy that can apply acupressure to the acupoints of the arm of the user.

BACKGROUND

A sleeve is an accessory worn on a user's arm, and its main function is to prevent the arms of the user from getting tanned and sunburned when the user moves under the sun wearing short sleeves. Although a conventional sleeve can achieve the above-mentioned purpose, it does not have energy particles that can improve the blood circulation of the user. On the other hand, in the theoretical basis of traditional Chinese medicine, the human arm has multiple acupoints. A specific point in the meridian at which the body's blood is concentrated, transferred or accessed is often called an acupoint. Because the position of each acupoint is different, each acupoint has its own function.

The purpose of the conventional sleeve is only for protection from the sun, but because it is wrapped on the arm of the user, therefore, if the structure of the conventional sleeve can be improved such that the sleeve can apply acupressure on the above-mentioned acupoints during wear thereof, the economic value and health care function thereof may be greatly enhanced.

SUMMARY

Therefore, an object of the present disclosure is to provide an acupressure sleeve that can alleviate at least one of the drawbacks of the prior art.

According to the disclosure, an acupressure sleeve for applying acupressure to predetermined acupoints on an arm of a user includes a sleeve body and an acupressure unit. The sleeve body is configured to elastically and tightly press against the arm of the user when the acupressure sleeve is worn by the user. The sleeve body has a fiber substrate, and a plurality of far-infrared particles and a plurality of negative ion particles blended in the fiber substrate. The acupressure unit includes a plurality of acupressure protrusions protruding from the fiber substrate into an interior of the sleeve body and configured to apply acupressure to the arm of the user at positions respectively corresponding to the predetermined acupoints.

BRIEF DESCRIPTION OF THE DRAWINGS

Other features and advantages of the present disclosure will become apparent in the following detailed description of the embodiment with reference to the accompanying drawings, of which.

DETAILED DESCRIPTION

Figure 1:
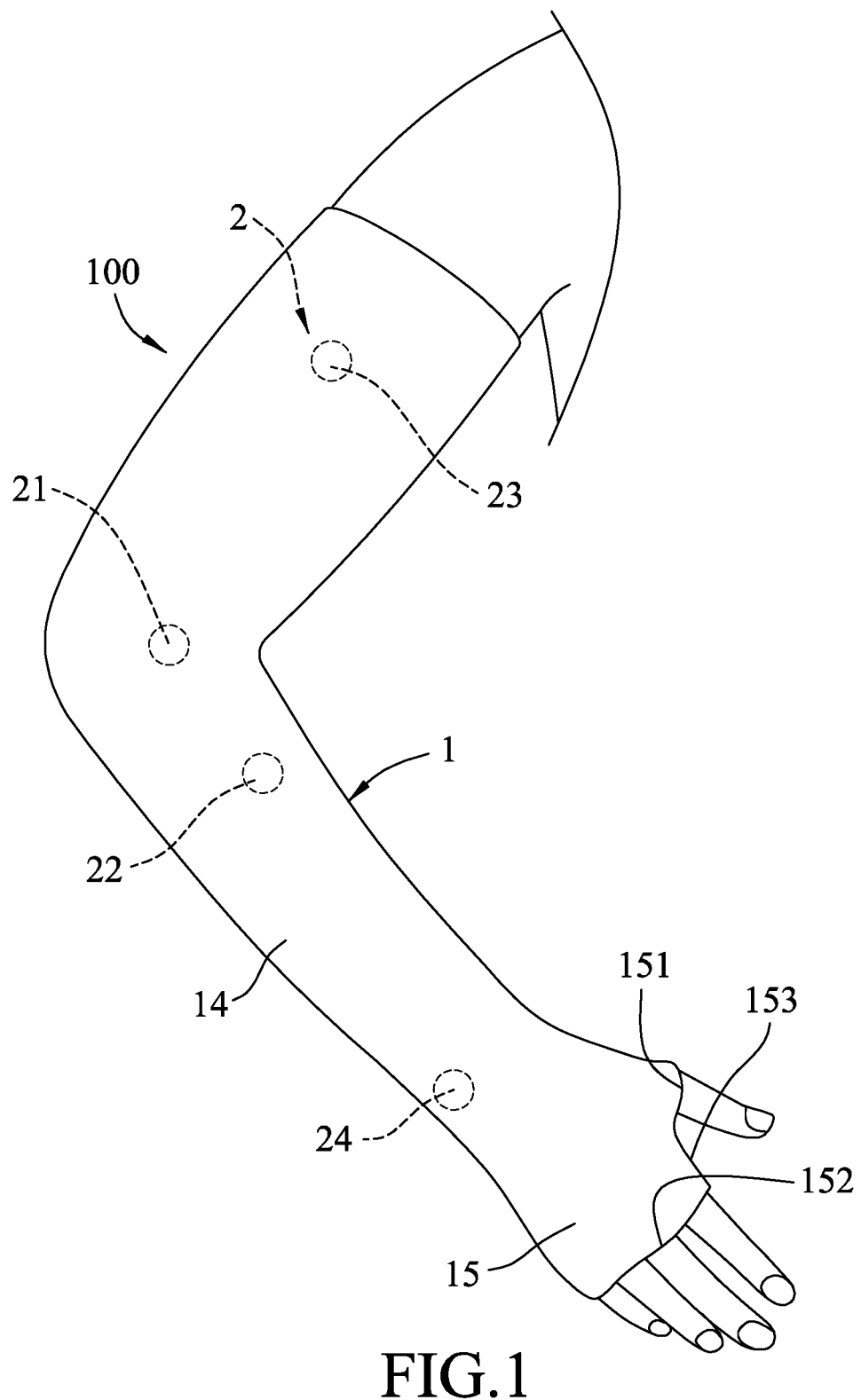
FIG. 1 is a schematic view of an embodiment of an acupressure sleeve according to the present disclosure in a state of use.
Figure 2:
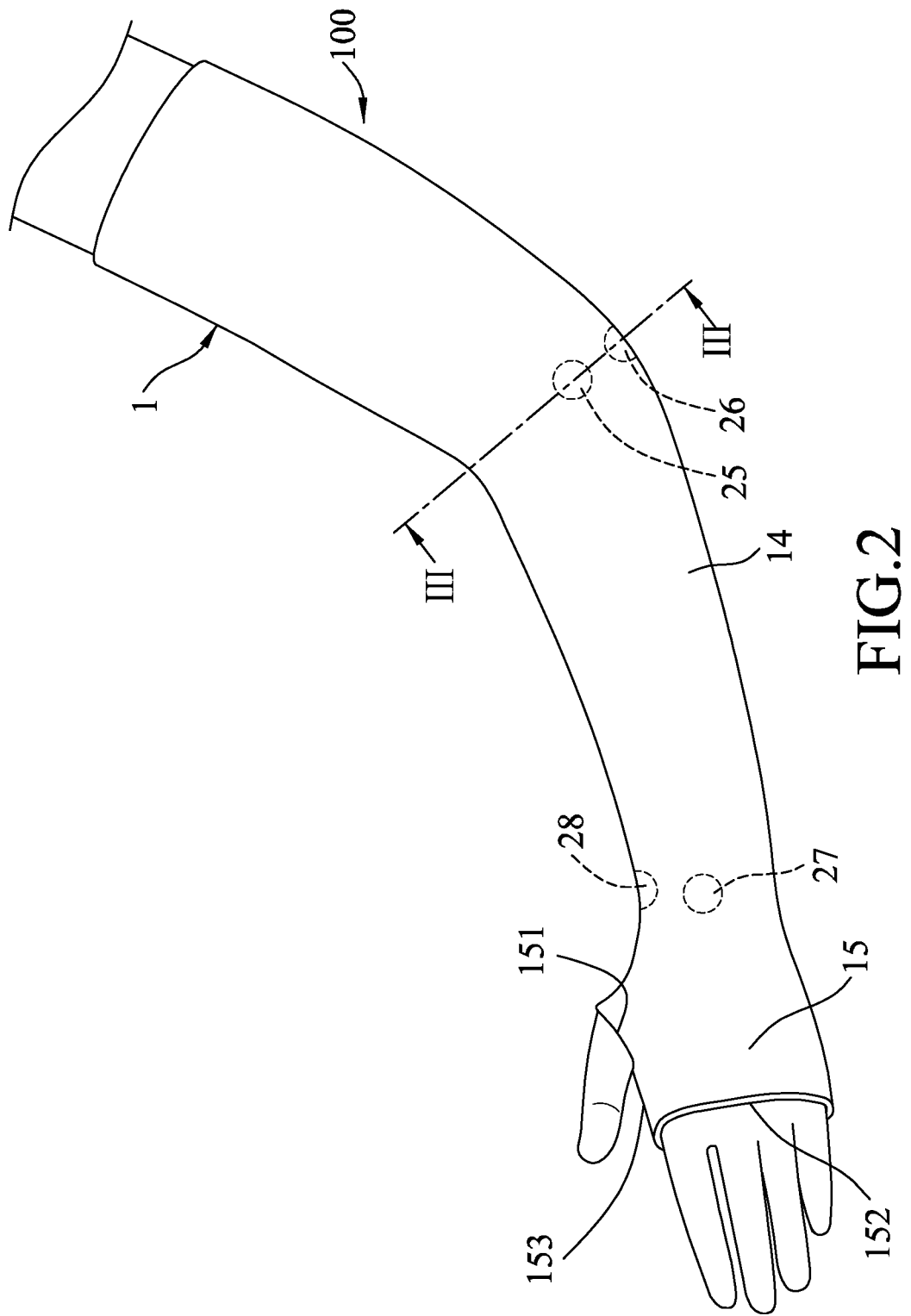
FIG. 2 is another schematic view of the embodiment taken from another angle.
Figure 3:
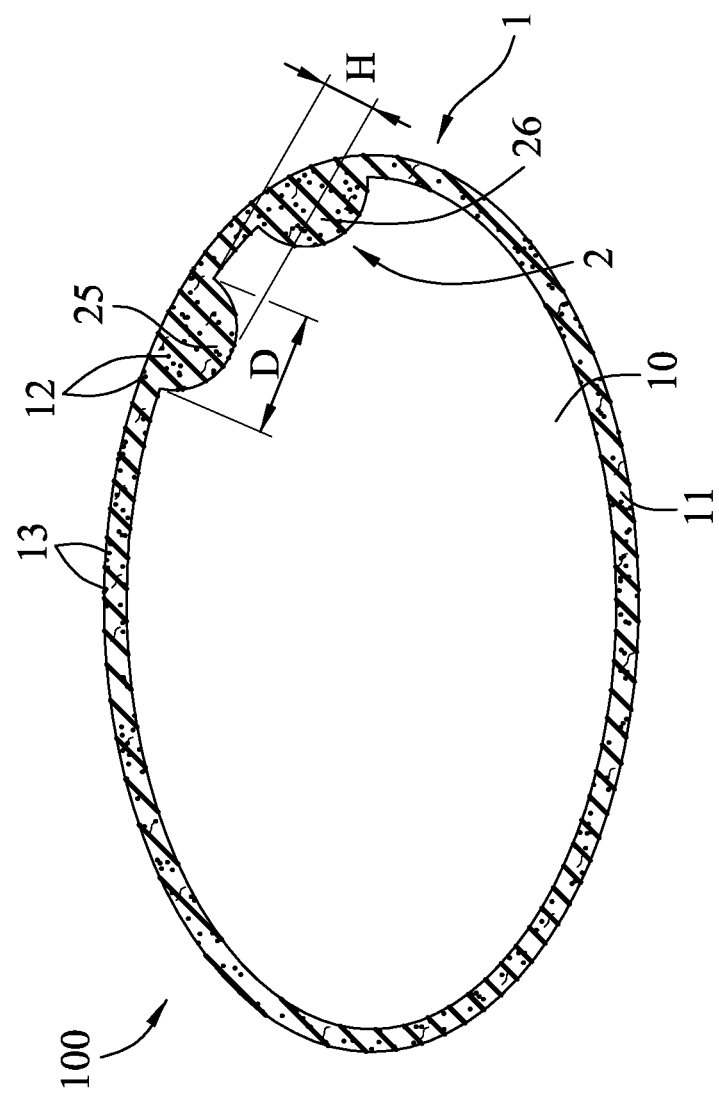
FIG. 3 is a sectional view taken along line III-III of FIG. 2.

Referring to FIGS. 1 to 3, an acupressure sleeve 100 for applying acupressure to predetermined acupoints on an arm of a user according to an embodiment of the present disclosure is shown to include a sleeve body 1 and an acupressure unit 2.

The sleeve body 1 is configured to elastically and tightly press against the arm of the user when the acupressure sleeve 100 is worn by the user. The sleeve body 1 is made by weaving far-infrared negative ion double-effect yarns with the blended yarn of peptide protein fibers and elastic fibers. In other words, the sleeve body 1 has a fiber substrate 11, and a plurality of far-infrared particles 12 and a plurality of negative ion particles 13 blended in the fiber substrate 11. If necessary, nano silver particles having a bactericidal effect may also be mixed with the fiber substrate 11. The chemical composition of the far-infrared particles 12 is 30% $Zn_2O$, 30% $Al_2O_3$, 30% $TiO_2$, and 10% $Sb_2O_3$. The far-infrared particles 12 can emit far-infrared light waves to resonate water molecules in the cells so as to stimulate cell activation and promote growth. That is, they can have the following effects: promote blood circulation and metabolism, activate cell tissues, discharge wastes and toxins from the body, balance the body's pH, increase oxygen content in the body to enhance immunity, quick drying of perspiration, remove odor, prevent mildew, kill bacteria, store heat and preserve warmth during winter. Thus, human health can be improved.

The negative ion particle 13 is usually a ring-shaped silicate mineral containing borons of Al, Na, Fe, Mg and Li. The main components are trigonal silicate, a small amount of iron oxide, aluminum oxide, magnesium, and organic matter. The negative ion particle 13 has the characteristics of adsorption, decomposition of hazardous substances, and air purification. The nano silver particle has a bactericidal function, and can bind to the cell wall or cell membrane of the bacteria so as to enter an interior of the cell body and block the metabolism of the cell, causing it to lose its activity and die naturally.

As distinguished by its appearance, the sleeve body 1 has an arm covering portion 14 for covering and tightening the arm of the user, and a hand covering portion 15 integrally connected to the arm covering portion 14 for covering the hand of the user. The hand covering portion 15 has a first through hole 151 for extension of the thumb therethrough, a second through hole 152 for extension of the four fingers therethrough, and a connecting section 153 that interconnects the first and second through holes 151, 152 and that covers the He Gu acupoint.

The acupressure unit 2 is integrally formed as one piece with the sleeve body 1, and is disposed on the arm covering portion 14, but is not limited thereto. The acupressure unit 2 includes a plurality of acupressure protrusions 21-28 protruding from the fiber substrate 11 into an interior 10 of the sleeve body 1 and configured to apply acupressure to the arm of the user at positions respectively corresponding to the predetermined acupoints. In this embodiment, as shown in FIG. 1, the acupressure unit 2 includes a first acupressure protrusion 21 corresponding to the Quchi acupoint, a second acupressure protrusion 22 corresponding to the Shousanli acupoint, a third acupressure protrusion 23 corresponding to the Binao acupoint, and a fourth acupressure protrusion 24 corresponding to the Yanglao acupoint. These acupoints 21-24 are located on the outer side of the arm. As shown in FIG. 2, the acupressure unit 2 further includes a fifth acupressure protrusion 25 corresponding to the Shaohai acupoint, a sixth acupressure protrusion 26 corresponding to the Xiaohai acupoint, a seventh acupressure protrusion 27 corresponding to the Neiguan acupoint, and an eighth acupressure protrusion 28 corresponding to the Lieque acupoint. The fifth and seventh acupressure protrusions 25, 27 are oriented towards the inner side of the arm. The sixth acupressure protrusion 26 is located on the lower side of the elbow, while the eighth acupressure protrusion 28 is located on the upper side of the wrist.

There is no special restriction on the shape and the protruding thickness of the first to eighth acupressure protrusions 21-28, as long as they protrude from the fiber substrate 11 into the interior 10 of the sleeve body 1, any shape thereof is acceptable. In this embodiment, each of the first to eighth acupressure protrusions 21-28 has a protruding curved surface, a protruding thickness (H) of 2 to 4 mm, preferably 3 mm, and a diameter (D) of 4 to 10 mm, preferably 5 mm.

Specifically, manufacturing process of the acupressure sleeve 100 of this embodiment uses a knitting machine in combination with a computer for controlling the knitting machine. That is, a design of the acupressure sleeve is inputted into the computer. With the computer controlling the knitting machine, a one-piece body of the acupressure sleeve 100 can be automatically formed, and there is no need for a second manufacturing process. This technique of combining the knitting machine with the computer is well-known in the art. Further, the first to eighth acupressure protrusions 21-28 are formed by thickening the yarns during the manufacturing process. Therefore, the manufacturing process of the acupressure sleeve 100 is relatively easy.

The first acupressure protrusion 21 is configured to apply acupressure to the Quchi acupoint, which is located on the opposite side of the elbow crease. Applying acupressure to the Quchi acupoint not only can lower blood pressure, treat joint pain, gastroenteritis, skin disease and allergic rhinitis, but also has obvious regulatory effects on the digestive, blood circulation and endocrine systems of the human body. The second acupressure protrusion 22 is configured to apply acupressure to the Shousanli acupoint, and is located about two inches below the first acupressure protrusion 21. The qi or energy of the large intestine channel of Hand Yangming is located at the Shousanli acupoint. Frequently applying acupressure to the Shousanli acupoint may alleviate abdominal distension, bowel obstruction, diarrhea, and other types of large intestine disorders. The third acupressure protrusion 23 is configured to apply acupressure to the Binao acupoint which is located on the lateral side of the arm at the end point of the deltoid muscle and on the line connecting the Quchi and Jianyu acupoints. By frequently applying acupressure to the Binao acupoint, apart from sculpting the muscles of the arms and getting rid of flabby arms, the effect of relieving pain in the shoulders may also be achieved. The fourth acupressure protrusion 24 is configured to apply acupressure to the Yanglao acupoint which is located at the back side of the ulna and above the ulnar styloid, which is the collection site of qi or energy of the small intestine channel of Hand Taiyang, and is closely related to the blood. By frequently applying acupressure to the Yanglao acupoint, the effect of relieving vision loss, eyeball congestion, acute lumbar sprain, neck stiffness and other symptoms may be achieved. The fifth acupressure protrusion 25 is configured to apply acupressure to the Shaohai acupoint which is located on the elbow crease. By applying acupressure to the Shaohai acupoint, elimination of excessive water to prevent edema of the arm, and the effect of treating schizophrenia, intercostal neuralgia, hand tremor, poor memory and insomnia may be achieved. The sixth acupressure protrusion 26 is configured to apply acupressure to the Xiaohai acupoint which is located at the small intestine channel of Hand Taiyang, which is located on the inner side of the elbow, and which is proximate to the Shaohai acupoint. Frequently applying acupressure to the Xiaohai acupoint may relieve headache, tinnitus and elbow pain. The seventh acupressure protrusion 27 is configured to apply acupressure to the Neiguan acupoint. The Neiguan acupoint is proximate to the palm. Specifically, the Neiguan acupoint is proximate to the horizontal line connecting the palm and the arm, and belongs to the pericardium meridian. The Neiguan acupoint is the site where the meridian qi and the collateral qi meet. By regularly applying acupressure to the Neiguan acupoint, the effect of treating heart, chest and stomach diseases may be achieved. The eighth acupressure protrusion 28 is configured to apply acupressure to the Lieque acupoint which is located on the upper part of the radial styloid process of the wrist. By applying acupressure to the Lieque acupoint, the effect of relieving cough, wheezing and headache may be achieved.

When the acupressure sleeve 100 of this embodiment is worn by the user, because the sleeve body 1 is made of an elastic material, it will tighten the arm to create a compression tightening effect. After wearing, since the hand wearing portion 15 can permit extension of the thumb and the four fingers of the hand therethrough and fix the wearing position thereof, the first to eighth acupressure protrusions 21-28 may respectively correspond to the important acupoints of the arm and may apply acupressure thereto for providing a therapeutic benefit to the user. In addition, the sleeve body 1 has the far-infrared particles 12 and the negative ion particles 13 which can generate energy waves. Therefore, through the presence of the far-infrared particles 12 and the negative ion particles 13 that generate energy waves, the body's blood circulation can be improved. Furthermore, by having the first to eighth acupressure protrusions 21-28, which protrude into the interior 10 of the sleeve body 1, the acupressure sleeve 100 of this disclosure can achieve the effect of applying acupressure to the important acupoints of the arm during wear thereof.

It should be noted herein that, since the first to eighth acupressure protrusions 21-28 of the acupressure unit 2 respectively correspond to the important acupoints of the arm of the user and protrude into the interior 10 of the sleeve body 1 to apply acupressure to these important acupoints, not only are the acupoints can be accurately pressed, the forces applied thereto are lighter as compared to manually pressing the acupoints.

Furthermore, the numbers and dispositions of the first to eighth acupressure protrusions 21-28 of the acupressure unit 2 are not limited to those as disclosed in this embodiment. The numbers thereof may be increased or decreased, and their dispositions may be varied according to the user's requirements. That is, the acupressure protrusions 21-28 of the acupressure sleeve of this disclosure may be disposed at positions corresponding to other acupoints on the arm of the user.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An acupressure sleeve for applying acupressure to predetermined acupoints on an arm of a user, comprising:
    a sleeve body configured to elastically and tightly press against the arm of the user when said acupressure sleeve is worn by the user, said sleeve body having a fiber substrate, and a plurality of far-infrared particles and a plurality of negative ion particles blended in said fiber substrate, said sleeve body being made by weaving far-infrared negative ion double-effect yarns; and
    an acupressure unit integrally formed as one piece with said sleeve body and including a plurality of acupressure protrusions protruding from said fiber substrate into an interior of said sleeve body and configured to apply acupressure to the arm of the user at positions respectively corresponding to the predetermined acupoints, said acupressure protrusions being formed by thickening said far-infrared negative ion double-effect yarns.

2. The acupressure sleeve as claimed in claim 1, wherein each of said acupressure protrusions has a protruding curved surface.

3. The acupressure sleeve as claimed in claim 1, wherein each of said acupressure protrusions has a protruding thickness (H) of 2 to 4 mm.

4. The acupressure sleeve as claimed in claim 3, wherein each of said acupressure protrusions has a diameter (D) of 4 to 10 mm.

5. The acupressure sleeve as claimed in claim 1, wherein each of said acupressure protrusions has a diameter (D) of 4 to 10 mm.

6. The acupressure sleeve as claimed in claim 1, wherein said sleeve body has an arm covering portion for covering the arm of the user, and a hand covering portion integrally connected to said arm covering portion for covering the hand of the user.

7. The acupressure sleeve as claimed in claim 6, wherein said hand covering portion has a first through hole for extension of the thumb therethrough, a second through hole for extension of the four fingers therethrough, and a connecting section interconnecting said first through hole and said second through hole.

8. The acupressure sleeve as claimed in claim 6, wherein said acupressure unit is disposed on said arm covering portion.

* * * * *